United States Patent
Henze et al.

(10) Patent No.: US 6,380,548 B1
(45) Date of Patent: Apr. 30, 2002

(54) METHOD AND DEVICE FOR DETECTING FOREIGN MATTER IN LONGITUDINALLY TRAVELING YARN

(75) Inventors: Herbert Henze, Mönchengladbach; Olav Birlem, Schwalmtal, both of (DE)

(73) Assignee: W. Schlafhorst AG & Co. (DE)

( * ) Notice: Subject to any disclaimer, the term of this patent is extended or adjusted under 35 U.S.C. 154(b) by 85 days.

(21) Appl. No.: 09/643,247

(22) Filed: Aug. 21, 2000

(30) Foreign Application Priority Data

Aug. 21, 1999 (DE) .......................................... 199 39 711

(51) Int. Cl.$^7$ .............................................. G01N 21/86
(52) U.S. Cl. ................... 250/559.4; 356/238.2
(58) Field of Search ........................ 250/559.4, 559.41, 250/559.45, 221, 223 R; 356/237.1, 238.1, 238.2, 238.3; 340/675, 676

(56) References Cited

U.S. PATENT DOCUMENTS

| 4,205,769 A | * | 6/1980 | Blitchington ................. 226/24 |
| 4,666,096 A | | 5/1987 | Heel et al. |
| 5,130,559 A | | 7/1992 | Leifeld et al. |
| 5,499,794 A | | 3/1996 | Aeppli ................. 250/559.45 |

FOREIGN PATENT DOCUMENTS

| DE | 3834478 | 4/1990 |
| DE | 3928279 | 2/1991 |
| DE | 4131664 | 3/1993 |
| DE | 4414517 | 12/1994 |
| DE | 19614026 | 10/1997 |
| EP | 0399945 | 11/1990 |
| EP | 0578975 | 6/1993 |
| EP | 0643294 | 3/1995 |
| WO | WO 97/36032 | 10/1997 |

* cited by examiner

Primary Examiner—Que T. Le
(74) Attorney, Agent, or Firm—Kennedy Covington Lobdell & Hickman, LLP

(57) ABSTRACT

A method and device for detecting foreign bodies in longitudinally traveling yarn (1), wherein light is directed on the yarn (1) and is reflected by its surface. Light reflected by the yarn (1) is detected by a sensor and is converted into signals. Subsequently, an evaluation of the signals is performed by comparing the signals with predetermined criteria which distinguish typical properties of foreign matter classified as tolerable, such as shell particles, from other foreign matter, such as foreign fibers, which are classified as not tolerable. Depending on whether these criteria are met, a decision is made whether a yarn interruption is suppressed or performed. In this manner, the efficiency of the production process of textile machines, such as spinning or bobbin winding machines, can be improved, and the uniformity and stability of the yarn are increased.

9 Claims, 2 Drawing Sheets ations, lowers the efficiency of the yarn producing or processing operation. In addition, it is also disadvantageous that each yarn piecing or connection inevitably produces a relatively prominent thickened and/or weakened location in the yarn, which impairs the desired uniformity in strength and appearance of the yarn.

METHOD AND DEVICE FOR DETECTING FOREIGN MATTER IN LONGITUDINALLY TRAVELING YARN

CROSS REFERENCE TO RELATED APPLICATIONS

This application claims the benefit of German Application DE P 19939711.2 filed Aug. 21, 1999, herein incorporated by reference.

FIELD OF THE INVENTION

The present invention relates to a method and a device for detecting foreign bodies in longitudinally traveling yarn, and more particularly to such a method and device wherein light is directed on the yarn and is reflected by its surface, the reflected light is detected by a sensor and is converted into signals, the signals are subsequently evaluated and, depending on the outcome of this evaluation, an interruption of the yarn travel may be actuated.

BACKGROUND OF THE INVENTION

The fiber material supplied to a textile yarn spinning device can contain impurities, foreign materials and foreign fibers, which may lead to visible, undesired irregularities in the finished product and/or to improper or poor cohesion between the fibers and, in turn, may ultimately result in a yarn break during the subsequent finishing processes. Such foreign matter causes monetary losses in cases of inferior quality or waste goods, and in additional costs when increased production outlay is necessary, for example, in case replacement yarn must be produced or provided. It is therefore customary to employ devices by means of which such foreign matter can be removed from the yarn.

European Patent Publication EP 0 643 294 discloses a method for detecting foreign material in yarn, wherein the yarn is illuminated, the light reflected by the yarn is measured and the presence of a foreign material is inferred from a change in the reflected light. If a threshold value for lighter foreign materials is exceeded, or a threshold value for darker foreign materials is not reached, a foreign material signal is generated and a cleaning cut of the yarn is actuated to remove the affected section of yarn.

A device for the visual detection of impurities, foreign materials and foreign fibers in textile fiber materials is known from European Patent Publication EP 0 399 945 which generates an output signal for actuating a cleaning cut of the yarn in case of sudden color changes in the reflected light.

Changes in color, as well as changes in brightness or reflectivity, however, do not only occur because of foreign fibers but, with cotton yarns for example, also result from the presence of shell and stem particles, as well as leaf fragments, contained in the yarn along with the cotton fibers. When such foreign materials are detected, output signals are also transmitted to the yarn cleaner in order to actuate cleaning cuts of the affected yarn areas. Unfortunately, the proportion of such undesired plant components in the fiber material of yarns can be considerable, due to the already extensive and still increasing automation of the picking process when harvesting cotton, and the attendant factor that an insufficient consideration is often given to the optimal degree of ripeness of the cotton in determining the correct time for harvesting cotton. A portion of the foreign plant material remains in the fiber material and is supplied to the spinning station in spite of great cleaning efforts in the opening room and cleaning during carding. The foreign materials are ultimately detected in the yarn after spinning, resulting in a multitude of cleaning cuts being actuated. Each of the cleaning cuts requires the performance of a yarn piecing or connecting process. A large number of cleaning yarn cuts and yarn piecing operations, which in unfavorable circumstances may be increased if it is necessary to repeat any of the individual piecing oper

OBJECT AND SUMMARY OF THE INVENTION

It is accordingly an object of the present invention to reduce the above mentioned disadvantages and to improve yarn production and processing.

This objective is addressed by providing a method and a device which basically classifies whether or not a foreign body in a yarn can be tolerated. More specifically, in accordance with the present invention, the method and device is adapted to detect foreign matter in a longitudinally traveling yarn and to either actuate or suppress an interruption of the yarn travel according to an evaluation of the detected foreign matter. For this purpose, the method and device utilize a light source for directing light on the yarn so as to be reflected thereby. The light reflected by the yarn is detected, e.g., by a suitable sensor, and signals representative of the reflected light are generated. Certain criteria are predetermined which distinguish the typical properties of foreign matter which can be tolerated in the yarn from the respective properties of foreign matter which cannot be tolerated in the yarn. In the device of the present invention, this criteria is stored, e.g., in a data memory. The signals generated according to the light reflected by the traveling yarn are evaluated by comparing the signals with the predetermined criteria utilizing an evaluation unit connected with the data memory. In turn, a yarn interruption is either actuated or suppressed according to whether the predetermined criteria has been met.

The type and nature of a yarn interruption may take different forms. For example, a cleaning cut of the yarn, such as by a yarn cleaner device, is one contemplated form of a yarn interruption. In a spinning operation, the spinning process may also be interrupted, for example, by stopping the spinning rotor. By suppressing yarn interruptions, a yarn interruption is not triggered with every signal indicating foreign matter, and it is possible in this manner to noticeably reduce the number of cleaning cuts or other yarn interruptions, and in turn reduce the disadvantages caused by piecing or other yarn connections.

Reductions in the visible appearance or in the stability of the finished yarn product as a result of the presence of foreign matter can be negligibly small in certain circumstances, for example, in the case where the foreign matter which is detected is very small. If it will be possible to remove the foreign matter in the course of a subsequent production or processing operation, for example, by stripping the foreign matter at a guide eye, or by washing the foreign matter out of a fabric material, no reduction in quality or suitability of the yarn or the finished product to be made from the yarn, in particular the visual properties thereof, will occur. Such removable foreign materials are particularly suitable for classification as tolerable foreign matter. The criteria are advantageously established such that they define such foreign matter as being tolerable.

In case of a signal indicating a foreign matter is present, a yarn interruption is preferably suppressed if several criteria are simultaneously met at one lengthwise location of the yarn in the detection area. In particular, for example, even though the detected brightness of the light reflected by the yarn may deviate from a predetermined reference value by more than a predetermined amount, if this brightness deviation does not occur for greater than a predetermined length of the yarn, while at the same time a variation of the brightness signal is detected in the affected longitudinal area of the yarn having the brightness deviation, a yarn interruption may be suppressed because, for example, such criteria may indicate the characteristic or typical range of brightness or color values for shell particles. A high degree of dependability in detecting tolerable foreign matter can be achieved by means of meeting several criteria simultaneously. The dependability of detection of tolerable foreign matter can additionally be increased by continuously detecting the yarn diameter and evaluating it as an additional signal.

The values established for the predetermined criteria are preferably determined by means of yarn samples which are soiled by foreign matter, and the determined values are thereafter stored. For example, the yarn samples and the foreign matter contained therein can be examined by the same method and in the same device used in the continuing production and processing operation. Comparative tests with other detection and evaluation means, such as a CCD camera, can also be performed. The stored values can be used not only for the actual detection process, but again for later detection processes. Storage of the values can take place centrally in the form of a data bank, and can be employed for the detection of foreign matter at a plurality of work stations and machines.

The criteria can also be automatically changed in the course of the production process. For example, slow changes in brightness of the yarn can be removed, and the respective criteria and threshold values can be compensated.

A particularly advantageous embodiment of the present method is the examination of a detected color spectra. In the course thereof, the color spectrum of the light reflected by the yarn is examined, and this color spectrum is compared with stored color spectra of tolerable foreign matter. In case the examined color spectrum agrees or corresponds with one of these color spectra used as a predetermined criteria, the presence of tolerable matter is assumed, and a yarn interruption because of this foreign matter signal is suppressed. This method is especially dependable and well suited for making a distinction between foreign matter which cannot be tolerated and which for example are to be removed by a cleaning cut, and tolerable foreign matter.

The device in accordance with the invention has at least one light source, a sensor, an evaluation device, and means for yarn interruption. The evaluation device is connected to a data memory. The predetermined criteria are advantageously stored in the data memory. A comparison of the signals with the predetermined criteria is preferably performed by means of the evaluation device, and the means for yarn interruption can be controlled as a function of the result of the comparison. A tolerable foreign matter is detected in a particularly simple and dependable manner by means of a device designed in this manner, and can be distinguished from other foreign matter to be removed. In this manner, it is possible to suppress foreign matter signals which, in devices in accordance with the known prior art, lead to yarn interruptions.

A sensor designed as a CCD line sensor requires little space and provides substantially reliable measured results. Signal portions, which are detected in the edge area of the yarn and represent values as a function of the diameter, can be suppressed or separated with the CCD line sensor. In this manner, it is possible to prevent the effect of changes in the diameter of the yarn on the measured brightness values. Moreover, an extraordinarily high resolution of the detection range on the surface of the yarn can be achieved. It is also possible in this way to detect small foreign matter or the length of the foreign matter very dependably and exactly, since sufficiently strong contrasts in individual sensor elements occur even with changes caused by small foreign bodies, while a brightness measurement performed with only a single sensor element provides little contrast and the sensitivity of the measuring device is thereby limited.

In an embodiment of the device, at least one light source with a broad-band light spectrum is provided for light generation. While one sensor is sufficient for measuring brightness, at least two sensors are employed for detecting a color spectrum, or for example a CCD three-line sensor in order to have more than one color support point available in the determination of a color. The CCD three-line sensor with blue, green and yellow filtering is particularly well suited for a color determination with more than one color support point. In an alternative embodiment of the device, at least two light sources, each with a narrow-band light spectrum, are provided in place of one light source with a broad-band light spectrum. An operation with more than one color support point is also possible in this manner.

A white light LED may be used as the light source to provide a broad-band light spectrum and requires little structural space for installation in comparison with other broad-band light sources, which is of advantage in connection with the employment at textile machines with a plurality of work stations.

The invention can be advantageously employed with spinning machines and other yarn-processing machines, such as warping creels, weaving machines and doubling frames, for example.

The present invention makes possible in a simple manner an effective reduction of piecing operations and yarn connections, i.e., splices, which leads to an improvement of the yarn quality and to an increase of the efficiency of production processes in connection with yarn.

Further details, features and advantages of the present invention will be described and understood form the following disclosure of a preferred embodiment of the invention with reference to the accompanying drawing figures.

DETAILED DESCRIPTION OF THE PREFERRED EMBODIMENT

Figure 1:
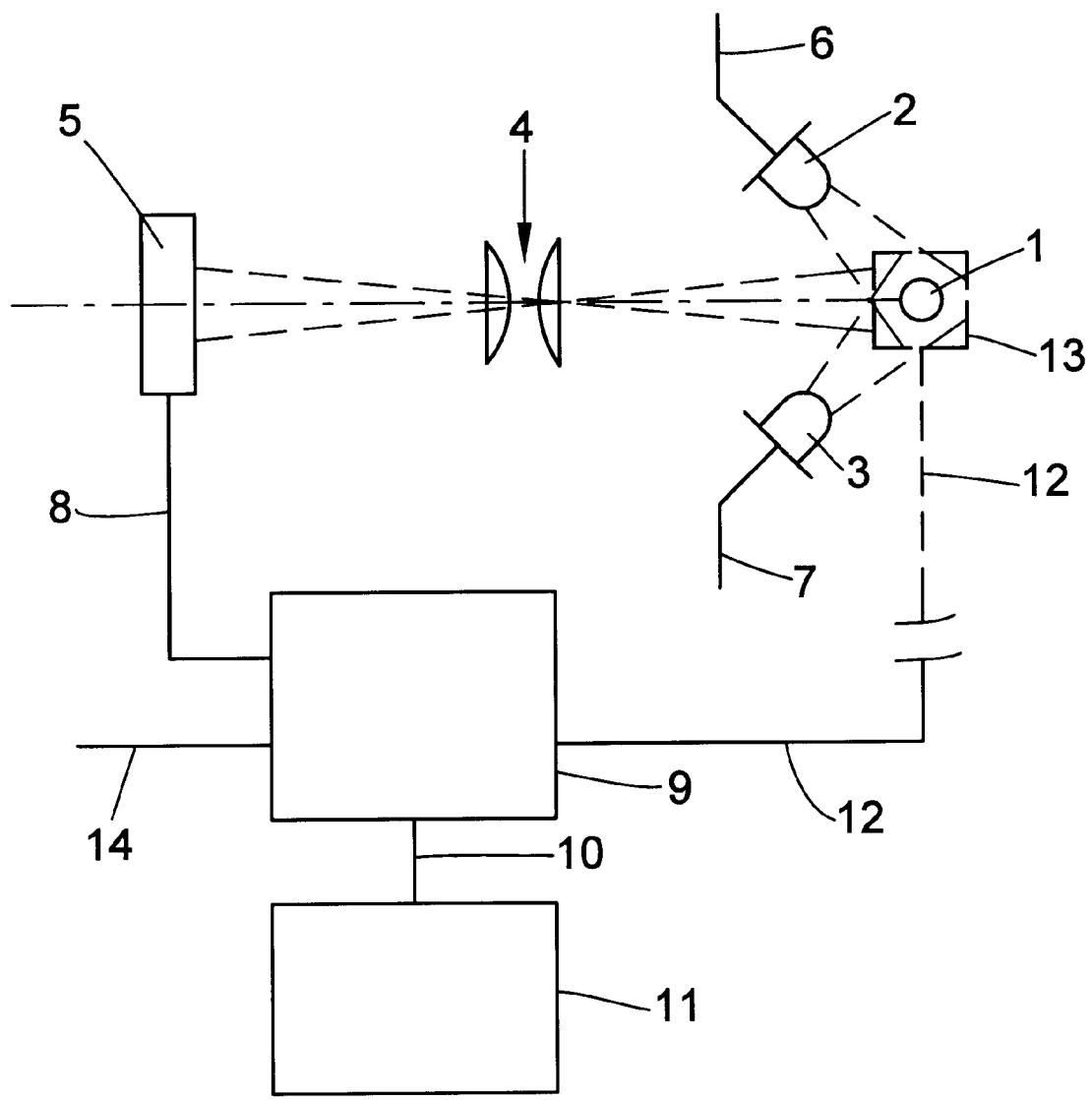
FIG. 1 is a schematic representation of a preferred embodiment of a device in accordance with the present invention.

Referring now to the accompanying drawings and initially to the schematic representation of FIG. 1, light is applied to a longitudinally traveling yarn 1, which is guided vertically in respect to the plane of the drawing representation, by two white light LEDs 2, 3 used as light sources. An optical device 4 is arranged in the beam path of the light reflected by the yarn 1 in such a way that the reflected light produces an image of the yarn 1 on the sensor 5 through the optical device 4. For further details, not represented for reasons of simplification, of such a measuring device and its place of employment, for example at a work station of a spinning or bobbin winding machine, reference is made to information in accordance with the prior art, which can be taken from the already mentioned documents of European Patent Publications EP 0 399 945 and EP 0 643 294. Lines 6, 7 serve as control and supply lines leading to the two white light LEDs 2, 3. The sensor 5 is connected via a line 8 with an evaluation unit 9 which is connected via a line 10 with a data memory 11. In an alternative embodiment of the device, the data memory 11 forms a structural unit with the evaluation unit 9. A further line 14 is used for data transfer between the evaluation unit 9 and other data processing installations or production elements, which are also not represented for reasons of simplification. A line 12 leads to a cutting device 13, which is used as means for yarn interruption and through which the yarn 1 passes.

The two white light LEDs 2, 3 apply a broad-band light spectrum to the yarn 1. The sensor 5 is embodied as a CCD three-line sensor. The arrangement illustrated in FIG. 1 permits a dependable determination of the brightness, and of brightness deviations, on the yarn surface passing through the detection area. Data, which define typical properties of foreign matter classified as tolerable, can be stored in the data memory 11. The data can be determined through the sensor 5 by means of yarn patterns soiled by foreign materials, and the detected values can thereafter be stored via the lines 8 and 10 and via the evaluation unit 9 in the data memory 11. The detected data can be called up from the data memory 11 via the line 14 and used for detecting foreign matter at a plurality of work stations and machines.

Figure 2:
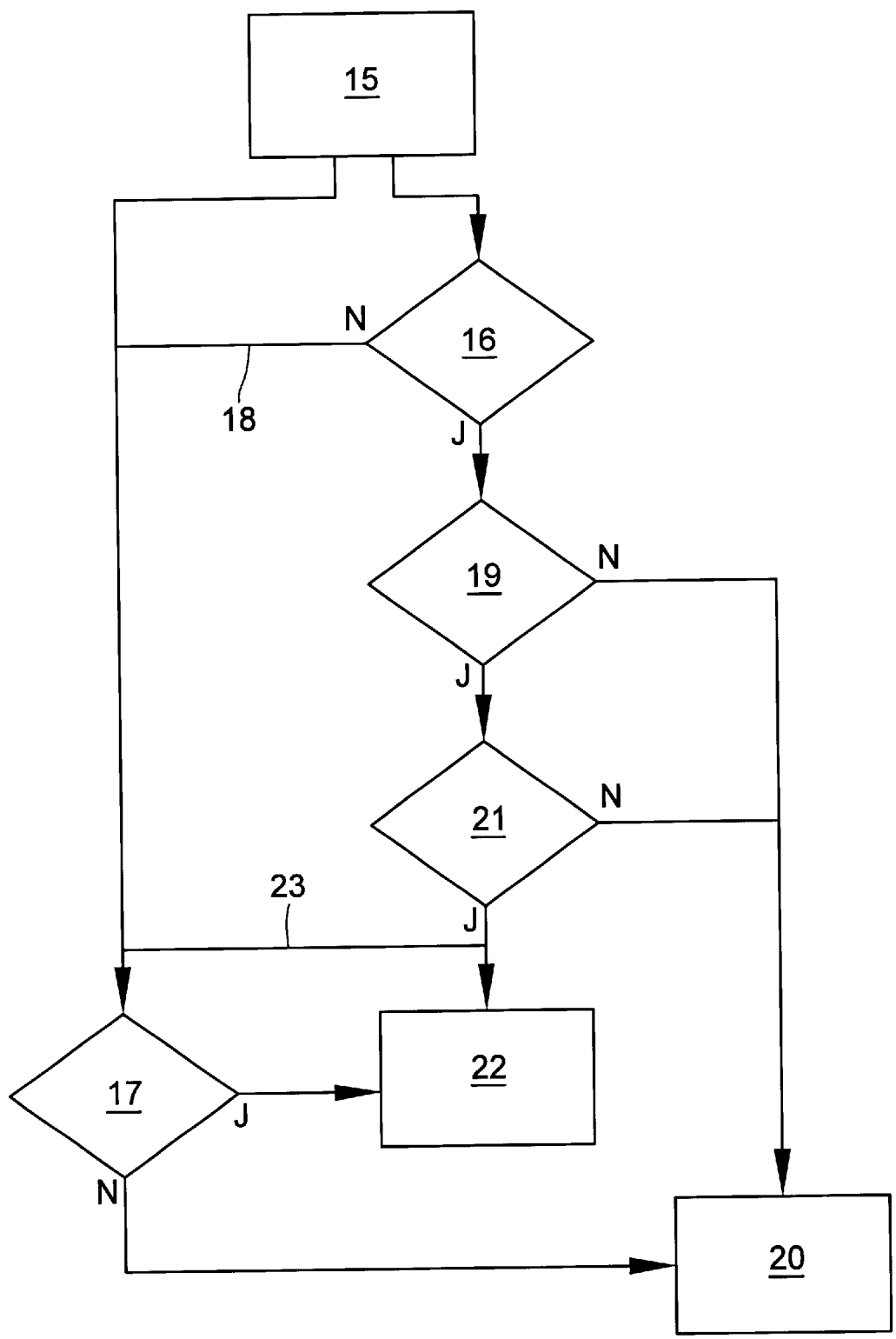
FIG. 2 represents a flow chart illustrating the method in accordance with the present invention.

The method of the present invention for detecting foreign bodies is represented by the flow chart of FIG. 2 and starts with a process step of a signal generation, indicated by the reference numeral 15. The light reflected by the yarn and detected by the sensor 5 is converted into signals in process step 15. In a further process step 16, the signals are subjected to a brightness examination. In the course of this step, a check is made whether the measured brightness lies outside of a predetermined tolerance range of a reference value. The tolerance range can be expressed in absolute values or by means of percentile values relating to the reference value. It is also possible to determine an upper or a lower threshold value. If the brightness lies within the tolerance range, or between the threshold values, the evaluation for the detection of foreign matter is either terminated or, alternatively, as indicated by the line 18, a check of the light spectrum is performed in a following process step 17. The results of individual process steps are indicated by j ("yes"), if criteria have been met, or by n ("no"), if criteria have not been met. If the brightness lies outside of the predetermined tolerance range, an examination of the lengthwise extent of the yarn affected by the brightness deviation, represented in process step 19, takes place after process step 16. In this examination of the lengthwise yarn extent, it is determined whether the lengthwise extent of the brightness deviation lies below a predetermined reference value. For example, 3 mm can be selected as the reference value. Depending on the requirements given, the reference value can also assume different values, for example 1 mm. If the lengthwise extent of the brightness deviation extends for a greater length than the predetermined reference value, a cleaning cut is triggered as process step 20. If the lengthwise extent of the brightness deviation extends for a lesser length than the reference value, a variation test 21 is performed.

In the variation test 21, an examination is made whether the brightness shows variations within its lengthwise extent or whether its value changes over such lengthwise extent. If no brightness variation or change in brightness value is detected, a cleaning cut of the yarn is triggered in process step 20. If there is a variation, a cleaning cut of the yarn is suppressed as process step 22. If there is a variation of the brightness value, it is alternatively possible to perform a check of the light spectrum in a subsequent process step 17, as indicated by line 23. Thus, a check of the light spectrum takes place either directly following the signal generation following process step 15, or alternatively following the detection of a brightness value outside of the predetermined tolerance and directly following the detection of a variation in the brightness value within the extent of the brightness deviation. In the course of a check of the light spectrum, the color spectrum of the light reflected by the yarn is determined. This color spectrum is compared with data of color spectra defining tolerable foreign matter, which are stored in the data memory 11. If the color spectrum agrees with at least one stored color spectrum used as the criteria, a cleaning cut of the yarn is suppressed in the subsequent process step 22.

The respective functions or checks performed in process steps 15, 16, 17, 19 and 21 can also be performed simultaneously, and the evaluation performed in parallel with these functions or subsequently thereto.

Data values used as criteria can be determined, for example, by means of yarn samples soiled by foreign materials and are subsequently stored. A further selection can be made according to data which only define foreign matter which can be removed in subsequent processing operations. These values can also be manually entered by means of a keyboard, not represented, or fed in through the line 14. The selection and determination of criteria or values can also be based on the experience of the operator, or can be influenced or adjusted according thereto.

A suppression of a yarn interruption, such as the suppression of a yarn cleaning cut, for example, and therefore the lowering of an undesired large number of piecing processes or yarn connections, is possible by means of the present invention in a large number of cases. The yarn quality can thereby be raised and the efficiency of production processes can be increased. As a result, the yarn production and processing operation is improved.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method for detecting foreign matter in a longitudinally traveling yarn, comprising the steps of:

directing light on the yarn to be reflected thereby, detecting the light reflected by the yarn and generating signals representative of the reflected light, predetermining of criteria which distinguish the respective properties of foreign matter which can be tolerated in the yarn from the respective properties of foreign matter which cannot be tolerated in the yarn, evaluating the signals by comparing the signals with the predetermined criteria, actuating a yarn interruption according to whether the predetermined criteria has been met.

2. The method in accordance with claim 1, wherein the predetermining of the criteria includes a determination of whether foreign matter can be removed during a subsequent processing operation.

3. The method in accordance with claim 1 or 2, wherein the predetermining of the criteria includes identifying a reference value for a brightness of light reflected by the yarn, the generating of signals representative of the reflected light includes producing brightness signals representative of the brightness of the reflected light, the evaluating of the signals includes comparing the brightness signals with the reference value, and the actuating of a yarn interruption includes suppressing a yarn interruption if a deviation of the brightness signals from the reference value by more than a predetermined value occurs along less than a predetermined length of the yarn and a variation of the brightness signal is detected along the length of the yarn having the deviation.

4. The method in accordance with claim 1, wherein the predetermining of the criteria includes sampling yarn soiled by foreign bodies and storing the results of the sampling.

5. The method in accordance with claim 1, wherein the detecting of the light reflected by the yarn includes detecting the color spectrum of light reflected by the yarn, the predetermining of the criteria includes predetermining and storing a color spectrum of light reflected by yarn having tolerable foreign matter, the evaluating of the signals includes comparing the detected color spectrum of reflected light with the predetermined and stored color spectrum, and the actuating of a yarn interruption includes suppressing a yarn interruption if the detected color spectrum of reflected light is within the predetermined and stored color spectrum.

6. A device for detecting foreign matter in a longitudinally traveling yarn, comprising:

a light source for directing light on the yarn to be reflected thereby, a sensor for detecting the light reflected by the yarn and means for generating signals representative of the reflected light, an evaluation device connected with a data memory containing predetermined criteria which distinguish the respective properties of foreign matter which can be tolerated in the yarn from the respective properties of foreign matter which cannot be tolerated in the yarn, an evaluation device connected with the data memory for evaluating the signals by comparing the signals with the predetermined criteria, means for actuating a yarn interruption according to whether the predetermined criteria has been met.

7. The device in accordance with claim 6, wherein the sensor is a CCD line sensor.

8. The device in accordance with claim 7, wherein the sensor is a CCD three-line sensor with blue, green and yellow filtering.

9. The device in accordance with claim 6, wherein the light source is a white light LED.

* * * * *